(12) United States Patent
Sekiguchi et al.

(10) Patent No.: US 11,648,065 B2
(45) Date of Patent: May 16, 2023

(54) CENTRALIZED CONTROL APPARATUS AND INSTRUMENT OPERATION METHOD

(71) Applicant: OLYMPUS CORPORATION, Hachioji (JP)

(72) Inventors: Kiyoshi Sekiguchi, Hachioji (JP); Yorito Maeda, Kiyose (JP)

(73) Assignee: OLYMPUS CORPORATION, Tokyo (JP)

( * ) Notice: Subject to any disclaimer, the term of this patent is extended or adjusted under 35 U.S.C. 154(b) by 715 days.

(21) Appl. No.: 16/682,366

(22) Filed: Nov. 13, 2019

(65) Prior Publication Data

US 2020/0138527 A1 May 7, 2020

Related U.S. Application Data

(63) Continuation of application No. PCT/JP2018/006734, filed on Feb. 23, 2018.

(30) Foreign Application Priority Data

May 25, 2017 (JP) .............................. JP2017-103365

(51) Int. Cl.
*A61B 34/00* (2016.01)
*A61B 90/35* (2016.01)
(Continued)

(52) U.S. Cl.
CPC .......... *A61B 34/25* (2016.02); *A61B 1/00006* (2013.01); *A61B 18/14* (2013.01); *A61B 90/35* (2016.02); *A61B 90/98* (2016.02); *A61M 13/003* (2013.01); *A61B 2018/00601* (2013.01); *A61B 2018/1412* (2013.01); *A61B 2034/252* (2016.02); *A61B 2034/254* (2016.02); *A61M 2205/502* (2013.01)

(58) Field of Classification Search
CPC . A61B 1/00006; A61B 1/00059; A61B 18/14; A61B 2018/00601; A61B 2018/1412; A61B 2034/252; A61B 2034/254; A61B 34/25; A61B 90/30; A61M 2205/502; G16H 20/40; G16H 40/60; G16H 50/70
See application file for complete search history.

(56) References Cited

U.S. PATENT DOCUMENTS

2005/0234326 A1 10/2005 Uchikubo et al.
2007/0191678 A1 8/2007 Sekiguchi

FOREIGN PATENT DOCUMENTS

EP 1 818 073 B1 9/2010
JP H07-160462 A 6/1995
(Continued)

OTHER PUBLICATIONS

Apr. 3, 2018 International Search Report issued in International Patent Application No. PCT/JP2018/006734.

*Primary Examiner* — Jon Eric C Morales
(74) *Attorney, Agent, or Firm* — Oliff PLC (57) ABSTRACT

A system controller can predict, when a first operation is performed on one device of a plurality of devices including a medical instrument, a subsequent operation that is the operation that occurs most frequently after the first operation based on an operation history information table in which past operation information is recorded for each procedure performed on the plurality of devices. This information can be displayed on an operation screen of an operation panel apparatus.

2 Claims, 10 Drawing Sheets

(51) Int. Cl.
*A61B 90/98* (2016.01)
*A61B 1/00* (2006.01)
*A61B 18/14* (2006.01)
*A61M 13/00* (2006.01)
*A61B 18/00* (2006.01)

(56) References Cited

FOREIGN PATENT DOCUMENTS

| | | |
|---|---|---|
| JP | H10-27089 A | 1/1998 |
| JP | 2000-259307 A | 9/2000 |
| JP | 2004-313341 A | 11/2004 |
| JP | 2005-287893 A | 10/2005 |
| JP | 2007-209626 A | 8/2007 |
| JP | 2008-026939 A | 2/2008 |
| JP | 2010-108388 A | 5/2010 |
| JP | 2010-170245 A | 8/2010 |
| JP | 2015-029791 A | 2/2015 |

| | NUMBER OF OPERATIONS | * | * | * | * | ... | * | * | * | * | ... | * | * | * | * | ... | ... | * | * | * |
|---|---|---|---|---|---|---|---|---|---|---|---|---|---|---|---|---|---|---|---|---|
| | CURRENT OPERATION | A | B | C | D | ... | A | B | C | D | ... | A | B | C | D | ... | ... | A | B | C |
| | OPERATION PERFORMED ONE OPERATION EARLIER | A | | | | | B | | | | | C | | | | | ... | A | | |
| | OPERATION PERFORMED TWO OPERATIONS EARLIER | A | | | | | | | | | | B | | | | | | | | |
| | ... | ... | | | | | | | | | | | | | | | | | | |
| | OPERATION PERFORMED N OPERATIONS EARLIER | ... | | | | | | | | | | | | | | | | | | |

TBL, x2, R, x1

FIG. 4

| OPERATION PERFORMED ONE OPERATION EARLIER | CURRENT OPERATION | NUMBER OF OPERATIONS |
|---|---|---|
| A | A | 0 |
|   | B | 6 |
|   | C | 1 |
|   | D | 0 |
| B | A | 5 |
|   | B | 0 |
|   | C | 0 |
|   | D | 0 |
| C | A | 0 |
|   | B | 0 |
|   | C | 0 |
|   | D | 1 |
| D | A | 1 |
|   | B | 0 |
|   | C | 0 |
|   | D | 0 |

TBL

↓ 「A」 ↓

| OPERATION PERFORMED ONE OPERATION EARLIER | CURRENT OPERATION | NUMBER OF OPERATIONS |
|---|---|---|
| A | A | 0 |
|   | B | 6 |
|   | C | 1 |
|   | D | 0 |
| B | A | 6 ← a |
|   | B | 0 |
|   | C | 0 |
|   | D | 0 |
| C | A | 0 |
|   | B | 0 |
|   | C | 0 |
|   | D | 1 |
| D | A | 1 |
|   | B | 0 |
|   | C | 0 |
|   | D | 0 |

TBL

FIG. 5

| USER NAME | PROCEDURE | OPERATION HISTORY INFORMATION |
|---|---|---|
| X | I | TBL1 |
|   | II | TBL2 |
|   | III | TBL3 |
|   | IV | TBL4 |
| Y | I | TBL5 |
|   | II | TBL6 |
|   | IV | TBL7 |
| Z | II | TBL8 |
|   | IV | TBL9 |
| W | I | TBL10 |
|   | II | TBL11 |
|   | V | TBL12 |
|   | VI | TBL13 |

CENTRALIZED CONTROL APPARATUS AND INSTRUMENT OPERATION METHOD

CROSS REFERENCE TO RELATED APPLICATION

This application is a continuation application of PCT/JP2018/006734 filed on Feb. 23, 2018 and claims benefit of Japanese Application No. 2017-103365 filed in Japan on May 25, 2017, the entire contents of which are incorporated herein by this reference.

BACKGROUND

Various medical instruments and various non-medical instruments can be installed in an operating room. In the various devices, various devices such as an operating light, an endoscope apparatus, a pneumoperitoneum apparatus, and an electrosurgical knife apparatus are included. Further, a surgical system can be used in which a system controller communicable with the various devices performs setting of a setting value and centralized control on the various devices.

An operation panel apparatus is connected to the system controller, and when surgery is started, an operator, a nurse, and the like can operate the operation panel apparatus, perform an execution instruction on a desired device, and perform setting and a change of various setting values, etc.

An operation on the device is an instruction of an execution or stop of functions included in the device, setting related to the functions, and the like. Further, a user of various devices such as an operator or a nurse can cause an operation screen for the operation to be displayed on the operation panel apparatus and perform a desired operation.

Further, with regard to the setting, the system controller having a preset function capable of setting a plurality of setting values collectively is also used.

For example, a system can have an execution history of a medical procedure of an image analysis performed in the past by the user stored in a storage section and when an interruption of a certain medical procedure occurs, a remaining order performed after an order in which an execution ends is specified based on the execution history.

SUMMARY

This application relates to a centralized control apparatus and a device operating method, and more particular to, a centralized control apparatus and a device operating method for predicting an operation on a device. A centralized control apparatus can include a processor, wherein the processor predicts, when a first operation is performed on one device of a plurality of devices including a medical instrument, an operation of which the number of performances is largest among operations performed next to the first operation as a second operation having a high possibility to be performed next to the first operation on the basis of past operation information for each procedure performed on the plurality of devices, and displays an operation screen for the predicted second operation on a display apparatus.

A device operating method can include predicting, when a first operation is performed on one device of a plurality of devices including a medical instrument, an operation of which the number of performances processor is largest among operations performed next to the first operation as a second operation having a high possibility to be performed next to the first operation on the basis of past operation information for each procedure performed on the plurality of devices; and displaying an operation screen for the predicted second operation on a display apparatus.

A device operating method can include predicting, when a first operation is performed on one device of a plurality of devices including a medical instrument, the second operation having a high possibility to be performed next to the first operation by using a neural network prepared on the basis of the past operation information performed on the plurality of devices; and displaying an operation screen for the predicted second operation on a display apparatus.

DETAILED DESCRIPTION OF THE PREFERRED EMBODIMENTS

Hereinafter, exemplary embodiments will be described with reference to the accompanying drawings.
(System Configuration)

Figure 1:
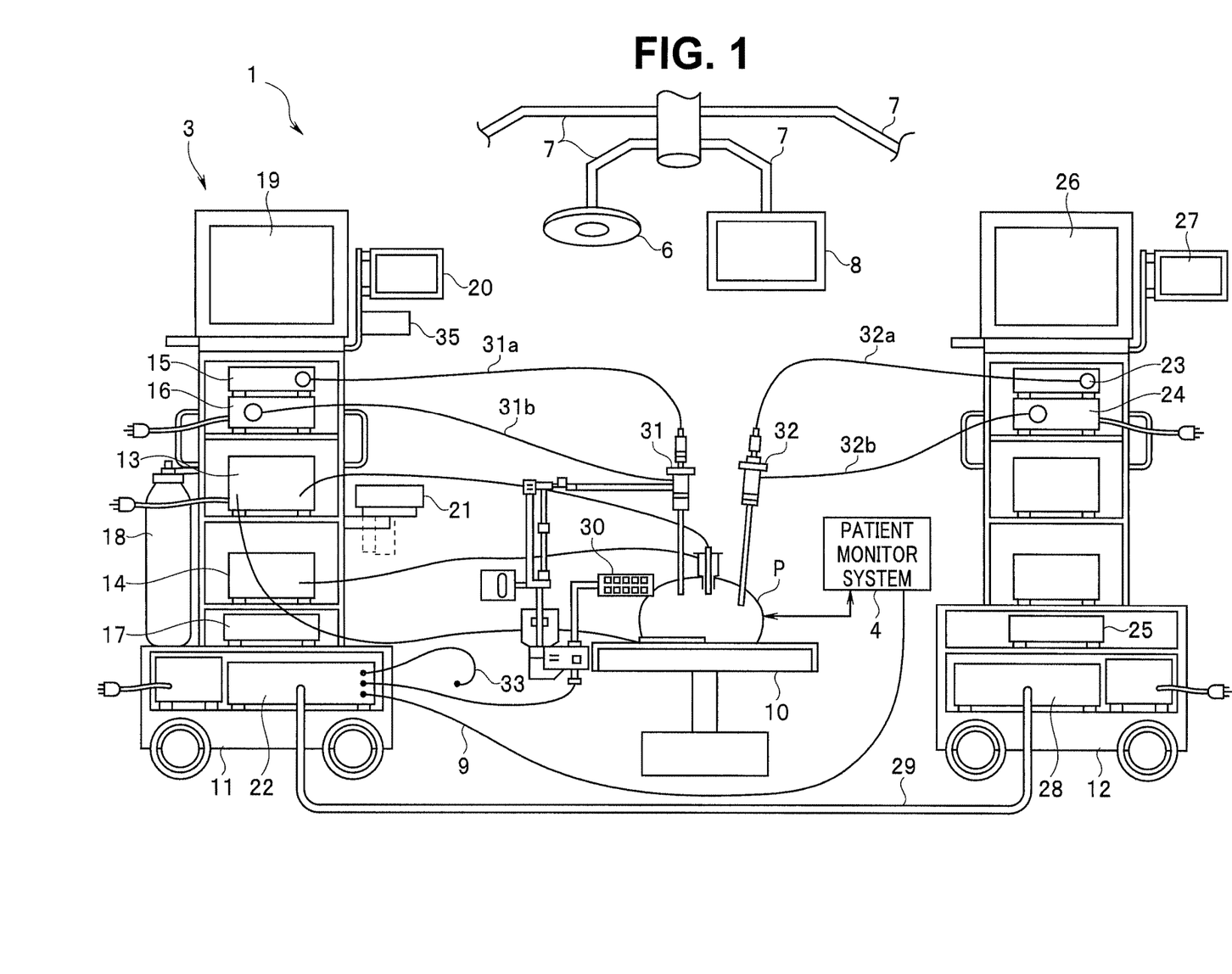
FIG. 1 is a configuration diagram of a surgical system 1 according to an exemplary embodiment.

First, the entire configuration of a surgical system 1 arranged in an operating room will be described with reference to FIG. 1. FIG. 1 is a configuration diagram of the surgical system 1 according to an exemplary embodiment. The surgical system 1 includes a plurality of medical instruments such as an endoscope and a plurality of non-medical instruments such as an operating light.

As shown in FIG. 1, a patient bed 10 in which a patient P lies, a plurality of operating lights 6, a display apparatus 8, and a medical system 3 are arranged in the operating room. The medical system 3 includes a first cart 11 and a second cart 12. Each of the operating lights 6 and the display apparatus 8 are fixed by arms 7 to a ceiling of the operating room.

As the medical instrument that is a controlled apparatus, for example, apparatuses such as an electrosurgical knife apparatus 13, a pneumoperitoneum apparatus 14, a video processor 15, a light source apparatus 16, and a recorder 17 for recording and a compressed gas cylinder 18 filled with carbon dioxide are mounted on the first cart 11. The video processor 15 is connected to a first endoscope 31 through a camera cable 31a.

The light source apparatus 16 is connected to the first endoscope 31 through a light guide cable 31b. Further, a display apparatus 19, a first centralized display panel 20, an operation panel apparatus 21, and the like are mounted on the first cart 11. The display apparatus 19 is, for example, a TV monitor that displays an endoscope image etc.

The centralized display panel 20 is display means capable of causing all data during an operation to be selectively displayed. The operation panel apparatus 21 is configured by a display section such as a liquid crystal display and, for example, a touch sensor integrally provided on the display section and is a centralized operation apparatus operated by a nurse or the like that is located in a non-sterilization area.

Further, a system controller 22 that is a centralized control apparatus is mounted on the first cart 11. Each of the above-described operating lights 6, the electrosurgical knife apparatus 13, the pneumoperitoneum apparatus 14, the video processor 15, the light source apparatus 16, and the VTR 17 are connected to the system controller 22 through a communication line (not shown). A headset-type microphone 33 is capable of being connected to the system controller 22 and the system controller 22 is capable of recognizing voices inputted from the microphone 33 and controlling each device by voices of operators.

Further, an RFID (Radio Frequency Identification) terminal 35 capable of wirelessly reading and writing individual ID information about things by an ID tag embedded in the first endoscope 31, a treatment instrument, etc. of the electrosurgical knife apparatus 13 is provided on the first cart 11.

On the other hand, a video processor 23 that is a controlled apparatus, a light source apparatus 24, an image processing apparatus 25, a display apparatus 26, and a second centralized display panel 27 are mounted on the second cart 12. The video processor 23 is connected to a second endoscope 32 through a camera cable 32a. The light source apparatus 24 is connected to the second endoscope 32 through a light guide cable 32b.

The display apparatus 26 displays an endoscope image etc. captured by the video processor 23. The second centralized display panel 27 is capable of selectively displaying all data during operations.

The video processor 23, the light source apparatus 24, and the image processing apparatus 25 are connected to a relay unit 28 mounted on the second cart 12 through a communication line (not shown). Further, the relay unit 28 is connected to the system controller 22 mounted on the above-described first cart 11 through a relay cable 29.

Thus, the system controller 22 is capable of centrally controlling the video processor 23, the light source apparatus 24, and the image processing apparatus 25 mounted on the second cart 12, the electrosurgical knife apparatus 13, the pneumoperitoneum apparatus 14, the video processor 15, the light source apparatus 16, and the VTR 17 mounted on the first cart 11, each of the operating lights 6, each of the display apparatuses 8, and an interior lamp (not shown). Therefore, in a case in which communication is performed between the system controller 22 and the above-described apparatuses, the system controller 22 is capable of displaying setting states of the connected apparatuses and setting screens of an operation switch etc. on the liquid crystal display of the above-described operation panel apparatus 21. Also, the system controller 22 is capable of performing an operation input of a change etc. in a setting value by contacting with a desired operation switch and operating a touch sensor in a predetermined area.

A remote controller 30 is a second centralized operation apparatus operated by a surgeon etc. located in a sterilization area and is capable of operating other apparatuses in which communication is established, via the system controller 22.

The system controller 22 is connected to a patient monitor system 4 through a cable 9 and the patient monitor system 4 is capable of analyzing biological information and causing the analysis result to be displayed on a required display apparatus.

Further, an infrared communication port (not shown) that is communication means is attached to the system controller 22. The infrared communication port is provided in a position easy to irradiate infrared light, such as the vicinity of the display apparatus 19 and is connected to the system controller 22 through a cable.

(Configuration of System Controller)

Figure 2:
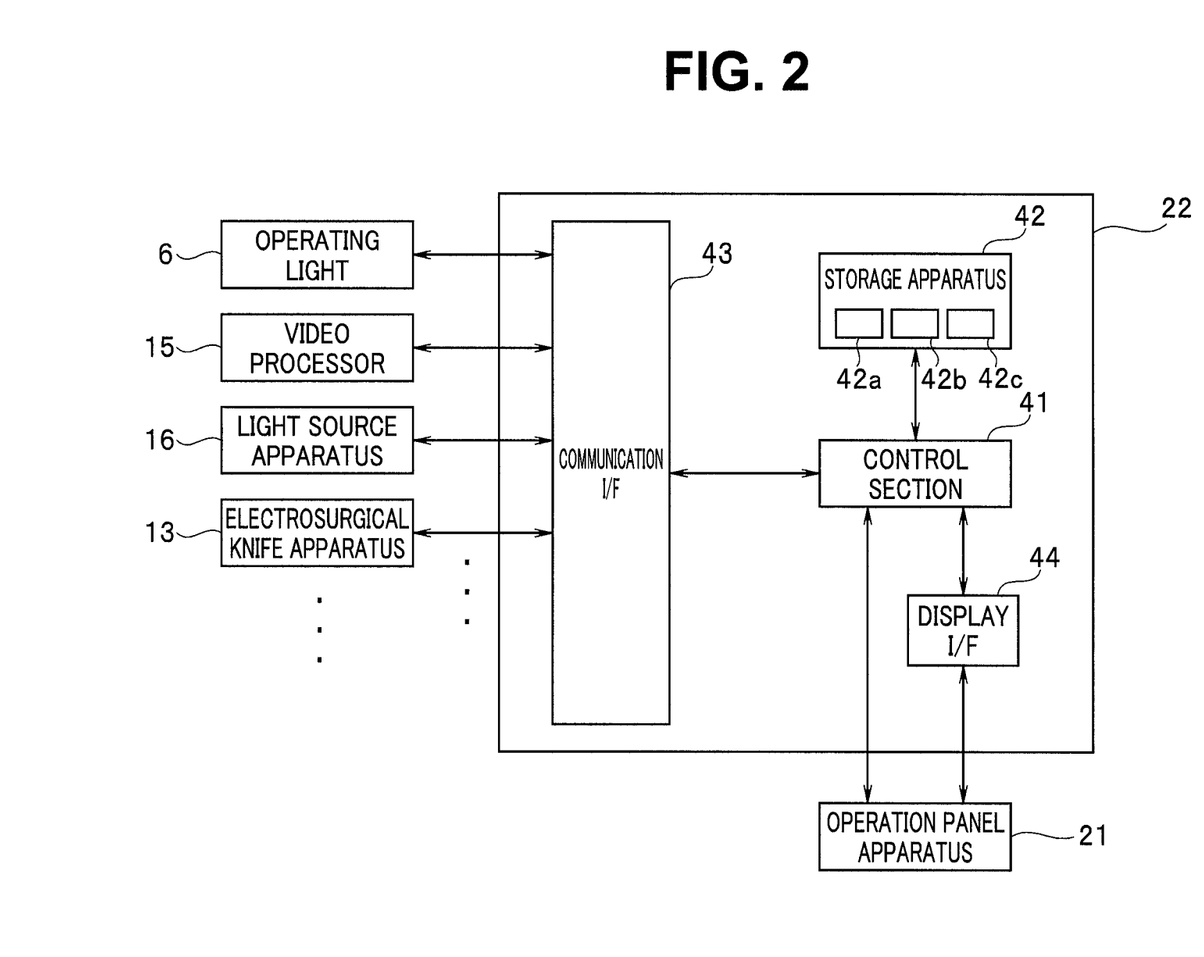
FIG. 2 is a block diagram showing a configuration of a system controller 22 according to an exemplary embodiment.

FIG. 2 is a block diagram showing a configuration of the system controller 22.

The system controller 22 includes a control section 41, a storage apparatus 42, a communication interface (hereinafter, abbreviated as a communication I/F) 43, and a display interface (hereinafter, abbreviated as a display I/F) 44.

The control section 41 includes a central processing unit (hereinafter, referred to as a CPU), a ROM, a RAM, and the like and the CPU reads and executes a software program of various functions recorded in the ROM to thereby realize various functions of the system controller 22.

The storage apparatus 42 is a nonvolatile rewritable memory storage such as a flash memory or a hard disk drive. A software program for various functions of the system controller 22 is also stored in the storage apparatus 42 and the CPU of the control section 41 can read and execute the software program.

Therefore, the storage apparatus 42 includes a program storage section 42a that stores a software program for various functions including a program for an operation support processing to be described later. The control section 41 and the storage apparatus 42 configure a processor that realizes various functions of the system controller 22. Note that, here, various functions are realized by a software program executed by the CPU, and further may be realized by an electronic circuit of an FPGA (Field Programmable Gate Array) or the like.

Further, the storage apparatus 42 includes a setting information storage section 42b that stores also various setting information of a plurality of devices to be described later. The control section 41 stores and sets various settings and setting values thereof inputted by a user in the setting information storage section 42b. At the same time, when causing each device to operate, the control section 41 controls an operation of each device by using the setting and setting values thereof stored in the setting information storage section 42b.

Further, the storage apparatus 42 includes a history information storage section 42c that also stores history information of an operation for a plurality of devices to be described later. A configuration of the history information storage section 42c will be described later.

The communication I/F 43 is an interface circuit in which communication lines to the plurality of devices are connected to each other and the control section 41 communicates with respective devices. In FIG. 2, the operating light 6, the video processor 15, the light source apparatus 16, and the electrosurgical knife apparatus 13 are shown among a plurality of devices. Therefore, the control section 41 communicates with the respective devices via the communication I/F 43 to thereby perform the setting and change in the setting values of the respective devices.

The control section 41 receives an operation signal from a touch panel of the operation panel apparatus 21. At the same time, the control section 41 outputs an image signal of an image displayed on the liquid crystal display of the operation panel apparatus 21 to the operation panel apparatus 21 via the display I/F 44.

An operator, a nurse, or the like (hereinafter, referred to as a user) operates the operation panel apparatus 21. Thereby, the user can perform instructions of operations and instructions of various settings of each medical instrument and each non-medical instrument of the surgical system 1.

The user can cause a home screen, a screen for the operation and setting of various devices, and the like to be displayed on a display screen of the operation panel apparatus 21. Further, the user can give a desired instruction from the system controller 22 to a desired device by touching various operation buttons displayed on the screen.

(Configuration of History Information Storage Section)

When a certain procedure is started, the user causes various devices to operate in a predetermined order. Further, while performing setting and change in the setting value, if necessary, the user performs an inspection and a procedure using the endoscopes 31 and 32, the electrosurgical knife apparatus 13, and the like.

When a target site of a treatment is, for example, upper gastrointestinal tract, a plurality of devices necessary for the inspection and the treatment of the upper gastrointestinal tract are used. Further, the user operates the operation panel apparatus 21 and issues an operation instruction to respective devices so that a device necessary for each scene from a start to an end of the procedure operates in the predetermined setting and setting value.

The history information about the operation instruction from a start to an end of surgery for each user and for each procedure is stored in the history information storage section 42c. When the procedure is started, recording of operation history information in the history information storage section 42c is also started.

Figure 3:
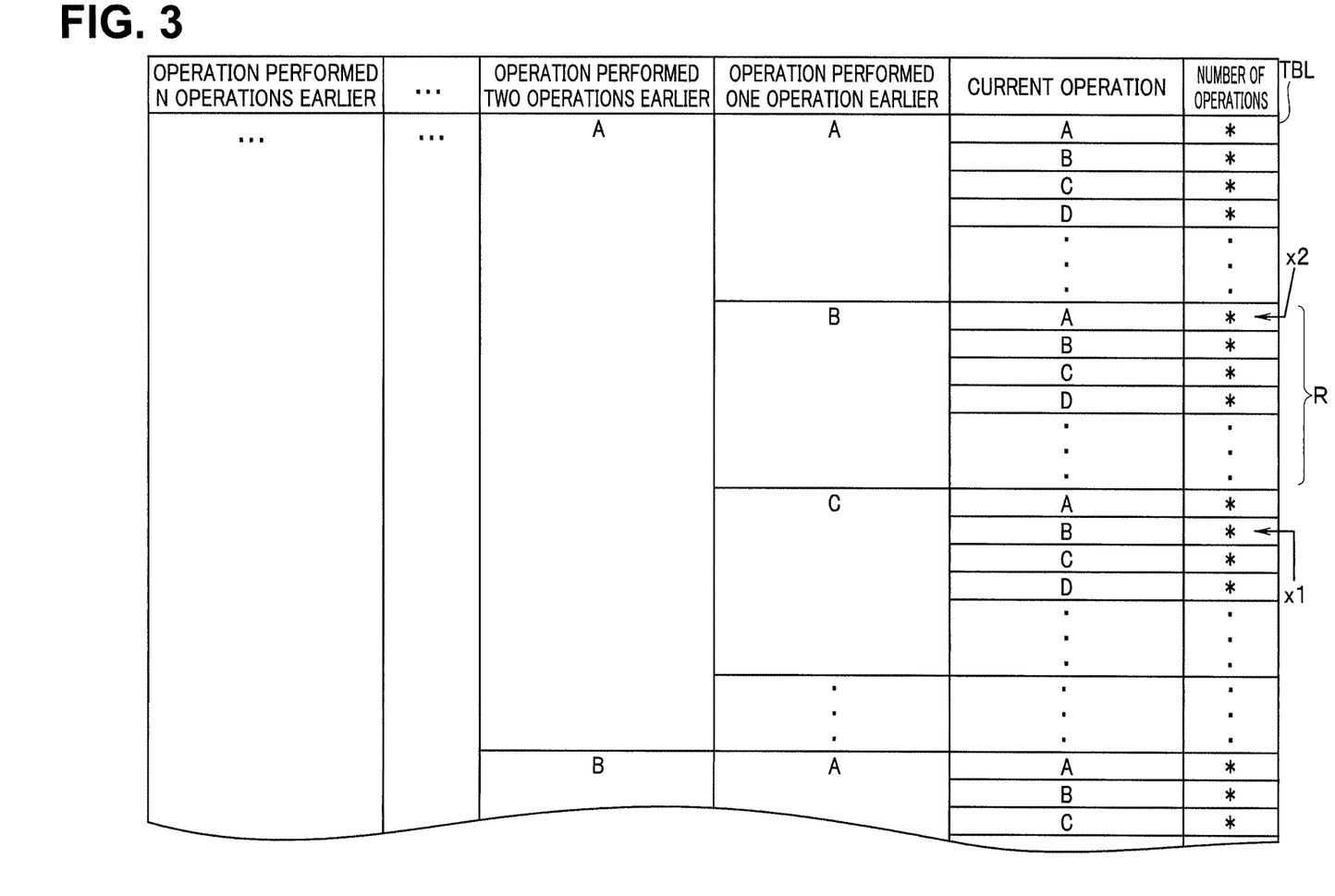
FIG. 3 is a diagram showing a configuration of an operation history information table TBL stored in a history information storage section 42c according to an exemplary embodiment.

FIG. 3 is a diagram showing a configuration of an operation history information table TBL stored in the history information storage section 42c.

Operation information about an operation performed on a device is stored in the operation history information table TBL shown in FIG. 3.

Here, the operation performed on a device is an operation instruction on the device (an execution instruction, a stop instruction, or the like), setting etc. of the output level, or the like. Specifically, the operation performed by the user relates to an operation instruction on the used device, setting of used functions from among a plurality of functions in the used devices, or the like. In FIG. 3, each operation data is shown in A, B, C, D, . . . .

The operation instruction is, for example, a stop instruction of air-blowing or a start instruction of air-blowing relating to an air-blowing function of the pneumoperitoneum apparatus 14, an execution instruction of a white balance function in the video processor 15, and a recording stop instruction or recording start instruction on the recorder 17 for recording.

The setting is, for example, setting of an air-blowing pressure and setting of an air-blowing rate of the pneumoperitoneum apparatus 14, or setting of brightness of a screen displayed on the display apparatus 19 of the video processor 15. Setting value data on the function may be included in the setting.

Therefore, the operation data is data on a start instruction of the operating light 6, data on an execution instruction of the white balance function of the video processor 15, data on a recording start instruction to the recorder 17, data on a setting instruction and setting value of the air-blowing rate of the pneumoperitoneum apparatus 14, or data on an adjustment instruction and setting value of a brightness adjustment of the video processor 15.

Accordingly, in a case in which setting of the setting value is performed with regard to setting of the operation, the operation data includes setting value data.

An operation data string includes a plurality of operation data arranged in the operated order. A plurality of operation data strings are capable of being stored in the operation history information table TBL as past operation information.

Specifically, the operation data string that is an array of the plurality of operation data arranged in the order of operations performed on a plurality of devices is recorded in the history information storage section 42c.

In FIG. 3, the operation information is recorded with a table format. The plurality of operation data strings are recorded in the operation history information table TBL as the operation information.

Each operation data string includes (N+1) operation data and data of the number of operations. N is an integer equal to or more than one. Each operation data string includes the plurality of operation data arranged in the order in which an operation is performed.

Accordingly, each operation data string includes the (N+1) operation data arranged in the order different from the orders of the other operation data strings. In FIG. 3, the number of performed operations shown in each operation data string is stored in "*" in a column of the number of operations.

Whenever the operation is performed, the number of operations is incremented by one in the operation data string that coincides with the (N+1) operation data of N operations earlier than the current operation plus the current operation.

For example, in a case in which an operation B is performed currently and the operation data string of the (N+1) operations including N operations earlier than the current operation plus the current operation is " . . . A, C, B", the number of operations of the operation data string shown in x1 of FIG. 3 is incremented by one.

Further, for example, in a case in which an operation A is performed currently and the operation data string of the (N+1) operations including N operations earlier than the current operation plus the current operation is " . . . A, B, A", the number of operations of the operation data string shown in x2 of FIG. 3 is incremented by one.

Note that, here, the plurality of operation data strings are recorded in the table data; further, a data format may be the other formats.

Figure 4:
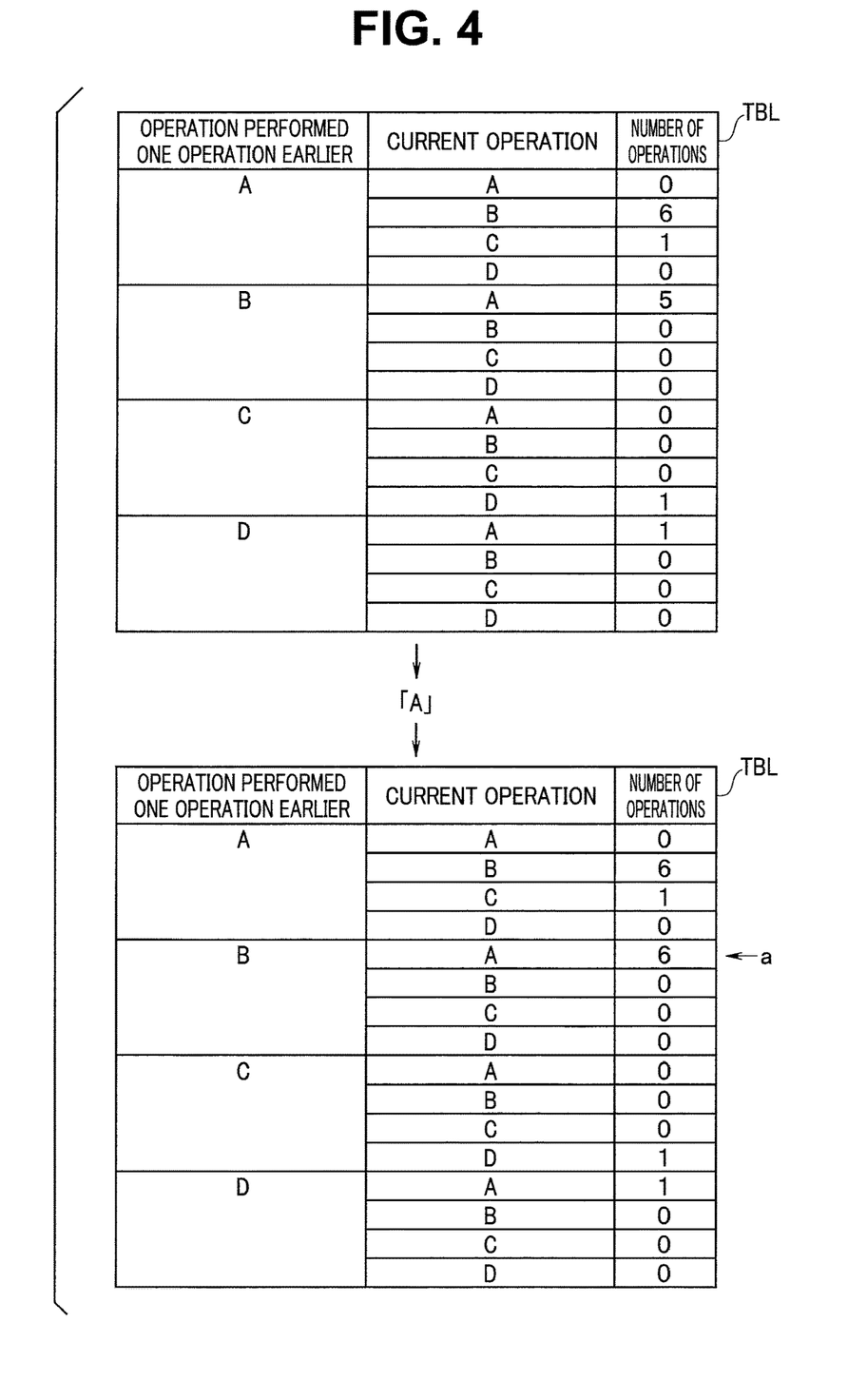
FIG. 4 is a diagram describing an updating of the number of operations according to an exemplary embodiment.

FIG. 4 is a diagram describing an updating of the number of operations. For ease of description, FIG. 4 shows the operation history information table TBL in which N is one and that has four functions.

FIG. 4 shows the numbers of operations of the operation history information table TBL in a case in which the operation is performed in the order of A, B, A, B, A, B, A, C, D, A, B, A, B, A, B.

As a result, for example, FIG. 4 shows that the number of performances of the operation "A" before the operation "A" is "0", the number of performances of the operation "A" before the operation "B" is "6", the number of performances of the operation "A" before an operation "C" is "1", and the number of performances of the operation "A" before an operation "D" is "0".

For example, when the operation history information table TBL shown in an upper stage of FIG. 4 stores "6" as the number of operations of a result in which the operation "B" is performed lastly. Afterwards, when the operation "A" is performed, the operation history information table TBL is updated to the number of operations shown in a lower stage of FIG. 4.

Specifically, the operation "A" is performed after the operation "B", and as a result, the number of operations of a position shown with an arrow "a" is incremented by one.

Thus, the number of operations for each operation data string showing the order of the operations performed in the past is stored and updated in the operation history information table TBL.

Accordingly, in each operation data string, the number of performances of operations, that is, information about the number of operations is stored as statistical data in the operation history information table TBL shown in FIG. 3. In other words, the operation data string includes the number of performances of operations for each order in which (N+1) continuing operations are performed.

As described above, whenever the operation is performed, the number of operations of the operation data string is updated in the operation history information table TBL corresponding to a procedure of the user. The number of operations for each operation data string is stored in the operation history information table TBL.

When the user such as an operator performs a certain procedure using the surgical system 1, the operation support is performed with reference to the operation history information table TBL.

Further, as described above, the operation history information table shown in FIG. 3 is provided for each user and for each procedure and is stored in the history information storage section 42c.

Figure 5:
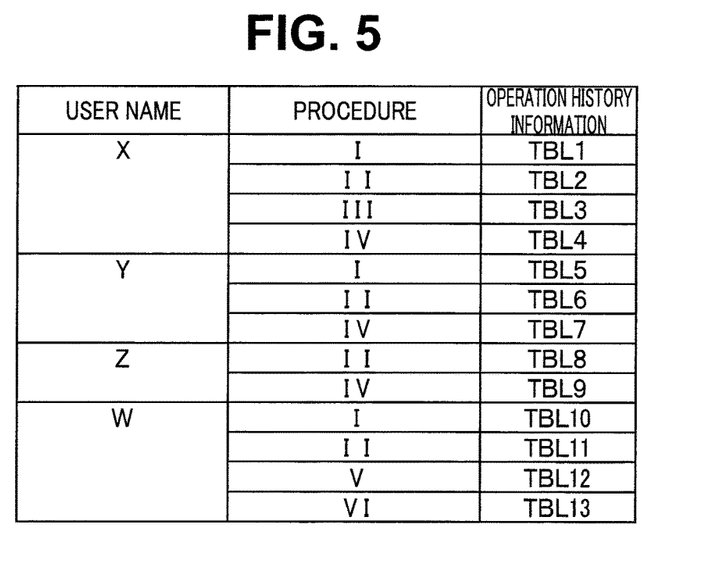
FIG. 5 is a diagram showing an example of a user-categorized operation history information table provided for each user and for each procedure according to an exemplary embodiment.

FIG. 5 is a diagram showing an example of a user-categorized operation history information table provided for each user and for each procedure.

As shown in FIG. 5, with reference to the user X, four operation history information tables TBL 1 to TBL 4 of four procedures I, II, III, and IV are stored in the history information storage section 42c. In the same manner, with reference to the user Y, three operation history information tables TBL 5 to TBL 7 of three procedures I, II, and IV are stored in the history information storage section 42c. With reference to the user Z, two operation history information tables TBL 8 and TBL 9 of two procedures II and IV are stored in the history information storage section 42c. With reference to the user W, four operation history information tables TBL 10 to TBL 13 of four procedures I, II, V, and VI are stored in the history information storage section 42c.

(Action)

Next, an action of the surgical system 1 will be described.

Figure 6:
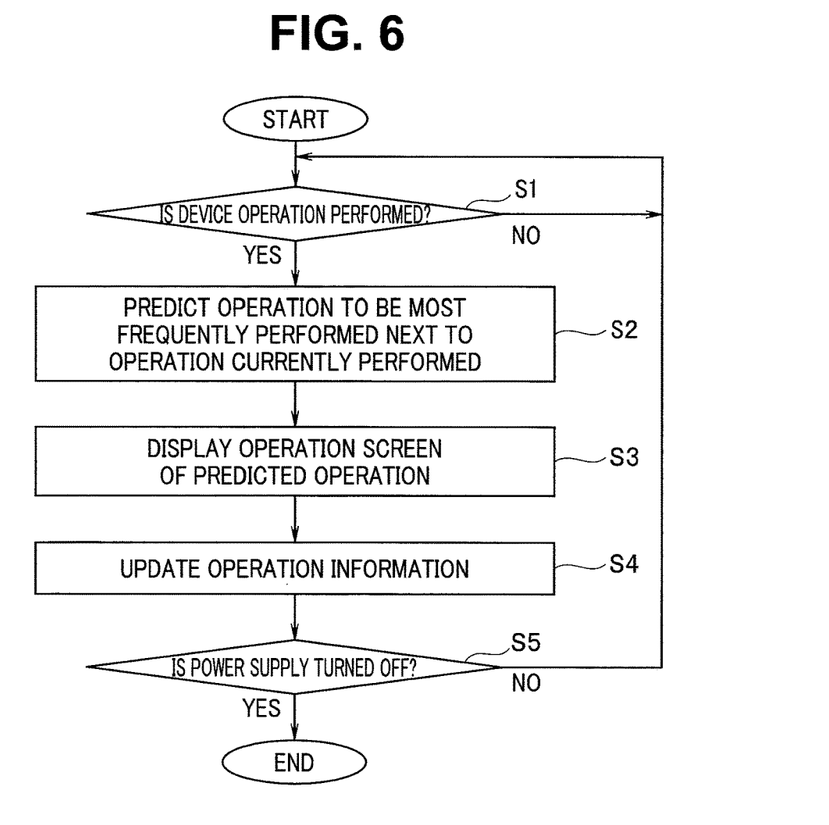
FIG. 6 is a flowchart showing an example of a flow of an operation support processing executed by a control section 41 according to an exemplary embodiment.

FIG. 6 is a flowchart showing an example of a flow of the operation support processing executed by the control section 41. When a procedure is started after a power supply is turned on, the control section 41 reads an operation support processing program from the program storage section 42a of the storage apparatus 42 and executes the process of FIG. 6.

The control section 41 determines whether or not the operation is performed on the operation panel apparatus 21 by the user, that is, determines whether or not a device operation is performed (step (hereinafter, abbreviated as S) 1). If the device operation is not performed (S1: NO), the processing is not performed at all.

If the device operation is performed (S1: YES), the control section 41 predicts an operation to be operated most frequently next to the operation performed currently with reference to the operation history information table TBL. Further, the control section 41 displays an operation screen of the predicted operation as an operation candidate screen to be performed next (S2, S3).

Concretely, the control section 41 predicts the most frequently performed operations after the present operation on the basis of the past operation information and displays an operation screen for the predicted operation on a screen of the operation panel apparatus 21.

For example, a case of FIG. 4 will be described as an example. The operation history information table TBL is supposed to have information about the numbers of operations shown in the lower stage of FIG. 4. Further, when the operation performed currently is the operation "B" and the "operation performed one operation earlier" is the operation "B", an operation of which the number of performances is largest among operations next to the operation "B" is the operation "A" as shown with the arrow "a". Therefore, the control section 41 predicts the operation "A" as an operation having a high possibility to be performed next and displays the operation screen of the operation "A".

In a case of FIG. 3, when the current operation is the "operation B", the control section 41 determines an operation of which the number of performances is largest on the basis of the operation history information table TBL from among the plurality of operation data strings (shown in R) before the (N+1) operations including the operation "B" as the "operation performed one operation earlier" and predicts the determined operation as an operation candidate to be performed next (S2). In the plurality of operation data strings described above, an operation of which the number of performances is largest as an operation next to the current operation is predicted as the operation candidate.

Specifically, in the process of S2, the operation performed most frequently among the operations performed next to the current operation "B" is predicted as an operation to be performed next on the basis of the past operation data recorded in the history information storage section 42c.

Further, the control section 41 displays the operation screen for the predicted operation on the operation panel apparatus 21 (S3).

From the above, when the first operation is performed on one device of a plurality of devices including medical instruments, the process of S2 configures an operation prediction section that predicts a second operation having a high possibility to be performed next to the first operation on the basis of the past operation information for each procedure performed on the plurality of devices.

Further, the process of S3 configures a display control section that displays an operation screen for the second operation predicted by the operation prediction section on the display apparatus.

The control section 41 updates the operation information about the operation history information table TBL on the basis of the present operation (S4).

Concretely, the control section 41 updates the number of operations of the operation history information table TBL on the basis of the operation in the process of S1. The updating of the number of operations is performed as described in FIG. 4.

The process of S4 configures an operation data recording section that records the operation data on the operation performed on the plurality of devices as the past operation information for each procedure.

The control section 41 determines whether or not a power supply of the system controller 22 is turned off (S5), and if the power supply is turned off, the process ends. If the power supply is not turned off, the process returns to S1 and the process from S1 to S5 is repeated.

Figure 7:
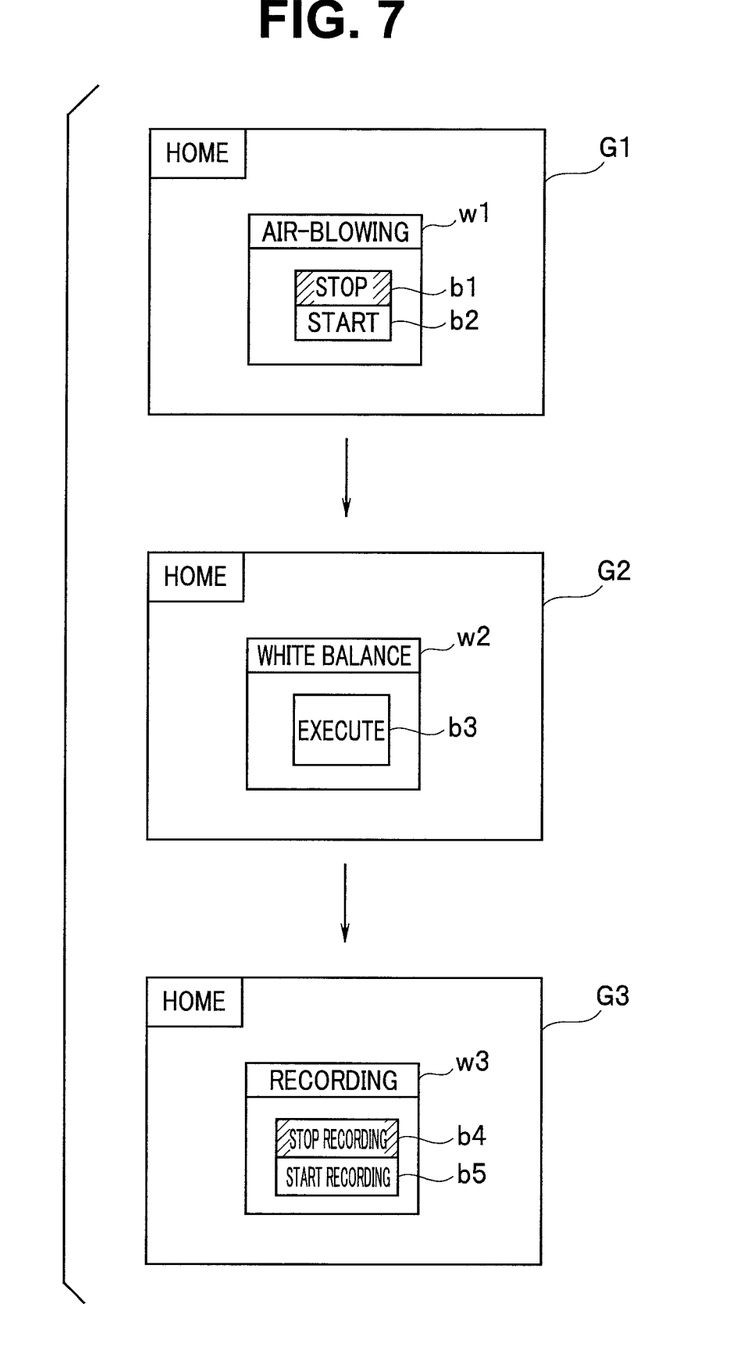
FIG. 7 is a diagram describing an example of a transition of an operation screen displayed on an operation panel apparatus 21 by repeating the process from S1 to S5 according to an exemplary embodiment.

FIG. 7 is a diagram describing an example of a transition of the operation screen displayed on the operation panel apparatus 21 by repeating the process from S1 to S5.

A screen G1 shown in FIG. 7 shows a screen for performing an operation relating to an air-blowing. An air-blowing operation window w1 and buttons b1 and b2 for stopping and starting the air-blowing function are displayed on the screen G1. A "stopping" state in the present state is shown by changing a color of the button etc. The "stopping" state in the present state is shown in an oblique line on the screen G1 shown in FIG. 7. The user is supposed to perform an operation relating to the air-blowing function by using the screen G1.

If the air-blowing function is operated (S1: YES), with reference to the operation history information table TBL, the control section 41 selects an operation of which the number of performances is largest, predicts the above operation as an operation having a high possibility to be performed currently, and displays an operation screen for the predicted operation on the operation panel apparatus 21 from among the plurality of operation data strings of the N operations that are performed earlier and include an operation of the "air-blowing function" as an "operation performed one operation earlier" (S3).

A screen G2 shown in FIG. 7 shows a screen for performing an operation relating to a white balance that is the predicted operation candidate. A white balance function window w2 and a button b3 for executing the white balance function are displayed on the screen G2. When the user performs an operation relating to the white balance function by using the screen G2, the operation information about the operation history information table TBL is updated (S4) and the process returns to S1.

Further, with reference to the operation history information table TBL, the control section 41 selects an operation of which the number of performances is largest, predicts the operation as an operation having a high possibility to be performed currently, and displays the operation screen for the predicted operation on the operation panel apparatus 21 from among the plurality of operation data strings of the N operations that are performed earlier and include the "white balance" as the "operation performed one operation earlier" (S3).

A screen G3 shown in FIG. 7 shows a screen relating to a certain recording that is the predicted operation candidate. A recording function window w3 and buttons b4 and b5 for recording stop and recording start are displayed on the screen G3. The "recording stop" in the present state is shown in an oblique line on the screen G3 shown in FIG. 7. When the user performs an operation relating to the recording function by using the screen G3, the operation information about the operation history information table TBL is updated (S4) and the process returns to S1.

Further, although not shown in FIG. 7, when the screen is a screen for setting the setting value, the user can operate the displayed screen and set a desired setting value.

Note that, as described above, when the operation corresponds to setting and is a setting operation of the setting value, the operation screen is a setting screen of the setting value. As described above, the operation data includes the setting value data, and therefore the setting value data included in the operation data is displayed as the setting value on the operation screen.

As described above, an operation screen to be displayed in the process of S3 is a screen for performing at least one of an instruction relating to executions of functions included in the device related to the predicted operation and a setting instruction relating to the functions.

Note that a "HOME" button for returning to the home screen is included in each of the screens from G1 to G3.

When the displayed candidate is not operated, the user can touch the "HOME" button and select the other operations. When a certain operation is performed on the device selected from the "HOME" button, the operation information is updated by the operation (S4).

As described above, when an operation is performed during the procedure, an operation screen for the operation of which the number of performances is largest statistically in the past is displayed on the operation panel apparatus 21 from the past operation information as an operation to be performed next to the operation performed currently in the procedure. Therefore, an operator or the like can perform a procedure smoothly.

Note that, in FIG. 7, only one operation screen is displayed on the operation panel apparatus 21; further, a plurality of operation screens of a plurality of operation candidates may be displayed on the operation panel apparatus 21.

Figure 8:
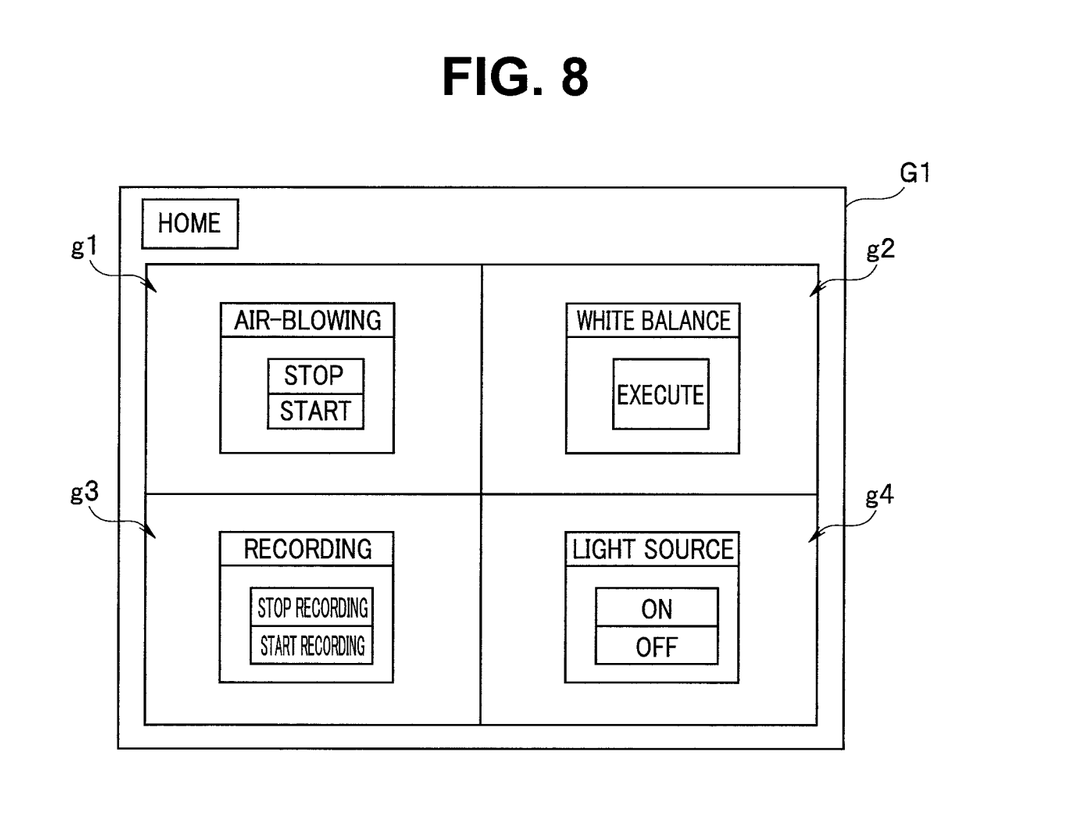
FIG. 8 is a diagram showing an example of a screen displaying an operation screen of a plurality of operation candidates according to an exemplary embodiment.

FIG. 8 is a diagram showing an example of a screen for displaying the operation screens of the plurality of operation candidates. Four operation screens from g1 to g4 are displayed on the screen G1 shown in FIG. 8. The screen g1 is an operation screen on which the number of operations is largest, the screen g2 is an operation screen on which the number of operations is largest next to the number of operations on the screen g1, the screen g3 is an operation screen on which the number of operations is largest next to the number of operations on the screen g2, and the screen g4 is an operation screen on which the number of operations is largest next to the number of operations on the screen g3.

Therefore, the user can perform an operation on an operation screen desired to be used from among the four screens.

Conventionally, the user such as an operator selects a screen of the function to be performed next from among menu screens etc. and causes the operation panel apparatus 21 to display the screen.

Figure 9:
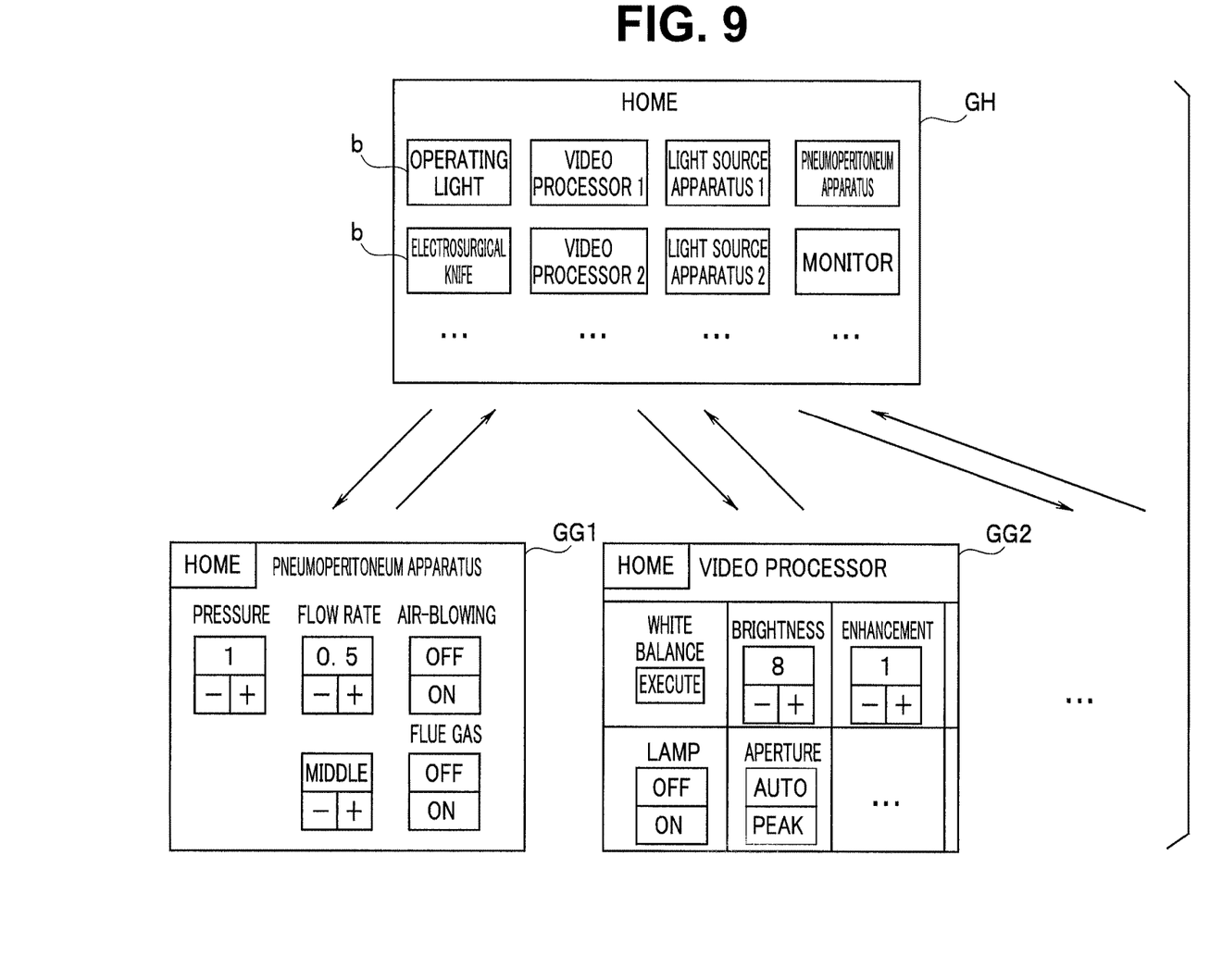
FIG. 9 is a diagram describing an example of a conventional transition of a screen displayed on the operation panel apparatus 21 according to an exemplary embodiment.

FIG. 9 is a diagram describing an example of a conventional transition of a screen to be displayed on the operation panel apparatus 21.

Conventionally, a plurality of selection buttons b for selecting a device that performs setting are displayed on the home screen GH. When the user selects a desired selection button b, an operation screen of the selected device is displayed on the operation panel apparatus 21. The user performs an execution, setting, or the like of the device by using the displayed operation screen. When an operation is performed on a device to be used next, the user always returns to the home screen GH, then selects a device to be used next, and performs the setting.

As shown in FIG. 9, the plurality of selection buttons b for devices are displayed on the home screen GH, and therefore the user has to select a desired button b from among the plurality of selection buttons b. Further, in a case in which the operation is performed on the next device after operating the selected device, the user has to return to the home screen GH again and start to operate a device selection.

In FIG. 9, there are shown a transition from the home screen GH to the screen GG1 of the pneumoperitoneum apparatus, a transition from the screen GG1 of the pneumoperitoneum apparatus to the home screen GH, a transition from the home screen GH to the screen GG2 of the video processor 15, and a transition from the screen GG2 of the video processor 15 to the home screen GH.

For example, when ten devices are provided and each device has ten functions, the user sets a certain function. In a case like this, after a device to be used is selected from among the ten devices, the user reads a setting screen for setting a function desired to be set from among the ten functions and afterwards performs the setting. Accordingly, conventionally, after returning to the home screen GH, the user has to perform the device selection, select a desired function from among the plurality functions of the selected device, and display the setting screen. Therefore, this is complicated for the user.

On the other hand, according to the present embodiment, when a certain operation is performed during the surgery in a certain procedure, an operation of which the number of performances is largest next to the number of performances of the operation is predicted as an operation having a highest possibility to be performed next. Since a screen for the predicted operation is displayed, the operator or the like can perform the procedure smoothly.

Particularly, when a certain function of a certain device is performed, an operation screen for the operation of the function is directly displayed on a display section of the operation panel apparatus 21, and therefore the user can perform the operation immediately.

(Modification 1)

In the above described embodiment, an operation data string including the (N+1) operation data is stored in the operation history information table TBL provided for each user and for each procedure. Further, when an operation to be performed next is predicted, use of the operation information up to any timing in the past may be enabled to be set. Specifically, a period of the past operation information to be used at the time of predicting the operation next to the operation performed currently may be enabled to be set.

As a period of the operation data to be used for the prediction, for example, a use of any one of the entire period in the past, one year in the past, a last one month, and the like may be enabled to be set.

Therefore, when the user sets a period of the operation data to be used as the operation information in the operation panel apparatus 21, the control section 41 deletes the operation data in which the period is passed from date information included in the operation data in the operation history information table TBL and updates the operation history information table TBL.

By using the operation data in a period arbitrarily set in this way, the user can adjust the operation support processing of the system controller 22 so that an optimum candidate is displayed for the user.

Note that a function capable of clearing the operation information in the operation history information table TBL may be provided.

(Modification 2)

In the above-described embodiment, the operation data of an operation on all the devices connected to the system controller 22 is used for the operation support processing. Further, the user may allow an operation that is not recorded in the operation history information table TBL to be set. Specifically, the user may allow a device that is not used for the prediction to be set as the past operation information to be used at the time of predicting an operation next to the operation performed currently.

Some functions that are not necessarily operated in this order each time are present among the operated devices. For example, a sound volume of a music player, an output value of the electrosurgical knife apparatus, or the like is operated only when the user feels discomfort at the present setting. When the operation data is included in the operation information, a prediction accuracy of the operation candidates to be performed next is caused to be reduced.

Therefore, reduction in an extraction accuracy of the function candidates to be performed next can be prevented so that an operation that is not recorded in the operation history information table TBL can be set.

As described above, according to the above-described embodiment and each modification, the centralized control apparatus and a device operating method that are intended to allow various operations to be performed in a procedure to be performed smoothly can be provided.

The operation having a high possibility to be performed next is predicted from the number of operations by using the operation history information table that stores the operation data string for N times of the operations performed in the past. Further, an operation candidate to be performed next can be predicted by using a machine learning method such as a neural network.

A surgical system according to the present embodiment has a configuration the same as the configuration of the surgical system 1 according to the first embodiment, and therefore descriptions are omitted.

A system controller can have a configuration substantially the same as the configuration of the previously described system controller 22. A neural network processing program can be stored in the program storage section 42a of the storage apparatus 42.

Figure 10:
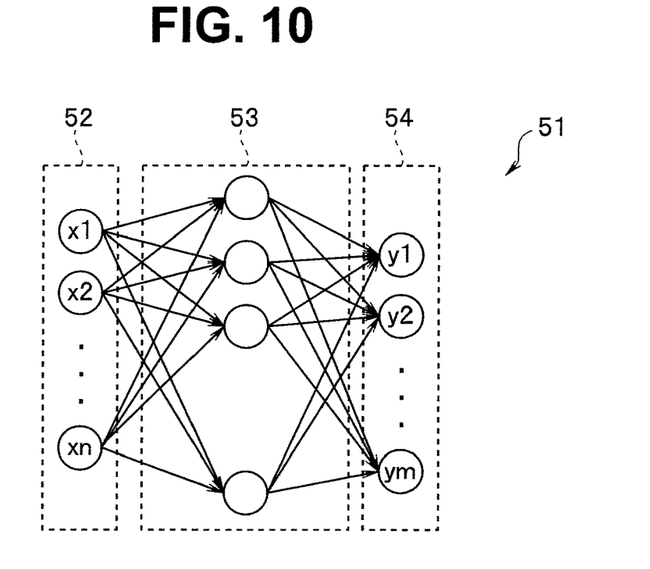
FIG. 10 is a model diagram showing a configuration of a neural network according to an exemplary embodiment.

FIG. 10 is a model diagram showing a configuration of the neural network.

The neural network 51 includes an input layer 52, an intermediate layer 53, and an output layer 54.

The input layer 52 has a plurality of input nodes. Here, the intermediate layer 53 has one stage including a plurality of intermediate nodes; further, may have a plurality of stages. The output layer 54 has a plurality of output nodes.

The neural network 51 has a configuration in which the each input node is connected to the each intermediate node and the each intermediate node is connected to the each output node.

For example, the operation relating data about the operated operation is inputted to the plurality of input nodes. The operating relating data is inputted to the input layer 52, for example, as in previous operation data inputted to an input x1, last but one operation data inputted to an input x2, a time interval between a previous operation and a last but one operation, . . . .

The plurality of output nodes output a probability estimated value to be performed next in each of the plurality of operations.

The each intermediate node of the intermediate layer 53 has, for example, a coupling weight etc. between the each input node and the each output node calculated by the machine learning method using the past operation history information.

The neural network 51 is generated for each user and for each procedure.

When the operation relating data including the operation performed currently is given to the plurality of input nodes, the probability estimated value for each operation is outputted to the each output node. The control section 41 determines an operation of the output node in which the output probability estimated value is highest as the operation candidate to be performed next.

Figure 11:
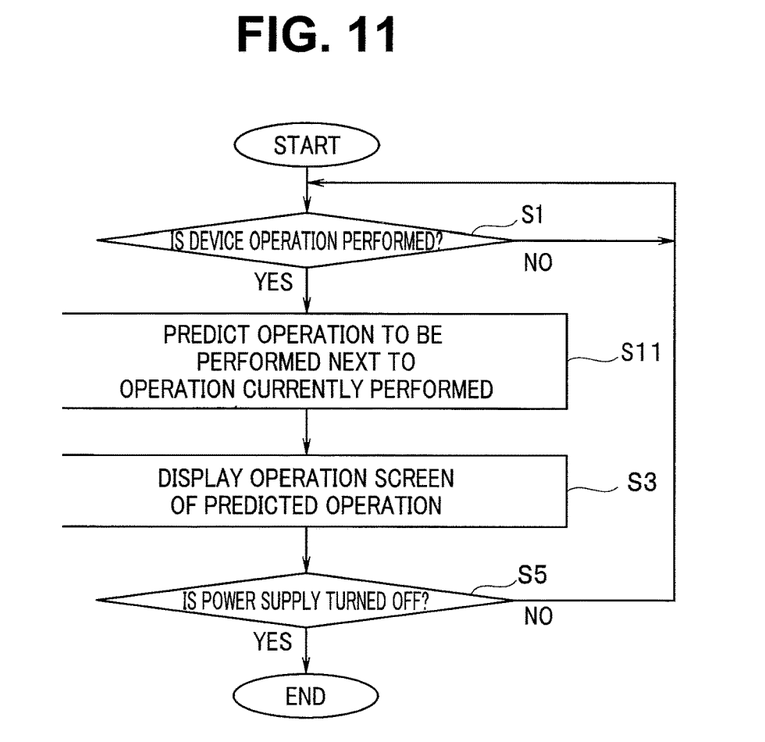
FIG. 11 is a flowchart showing an example of a flow of the operation support processing executed by the control section 41 using the neural network according to an exemplary embodiment.

FIG. 11 is a flowchart showing an example of a flow of the operation support processing executed by the control section 41 using the neural network according to the present embodiment. In FIG. 11, a step number is added to the same process as the process of FIG. 6 and descriptions are omitted.

FIG. 11 is the same as in the process of FIG. 6. Further, after the process of S1, the control section 41 predicts an operation to be performed next to the operation performed currently on the basis of the neural network (S11).

Specifically, when a first operation is performed on one device of a plurality of devices including medical instruments, the process of S11 configures an operation prediction section that predicts a second operation having a high possibility to be performed next to the first operation on the basis of the past operation information for each procedure performed on the plurality of devices. Particularly, the process of S11 configures the operation prediction section that predicts the second operation having a high possibility to be performed next to the first operation by using the neural network prepared on the basis of the past operation information performed on the plurality of devices.

Further, the control section 41 displays an operation screen of the predicted operation (S3). In FIG. 11, the updating processing of the operation history information about the process of S4 in FIG. 6 is not performed. The machine learning method for the neural network is performed differently.

Therefore, according to the present embodiment, the centralized control apparatus and the device operating method that are intended to be capable of smoothly performing various operations to be performed in a procedure can be provided.

The modification 1 and the modification 2 are also applicable to the present exemplary embodiment.

Further, a plurality of operation candidates may be displayed as shown in FIG. 8. In this case, the plurality of operation screens having a high probability estimated value are displayed.

An operation screen of an operation predicted to be performed next can be displayed on the operation panel apparatus 21 and the user touches a displayed button, and thereby instructs the operation to be performed. Further, according to a third embodiment, a display of the predicted operation screen and an execution of the operation are also automatically performed.

A surgical system according to the present embodiment has a configuration the same as the configuration of the surgical system 1 according to the first embodiment, and therefore descriptions are omitted.

A system controller according to the present embodiment also has a configuration substantially the same as the configuration of the previously described system controller 22.

According to the present embodiment, the processing program that uses the operation history information table TBL or the neural network processing program according to the second embodiment is stored in the program storage section 42a of the storage apparatus 42.

According to the present embodiment, a display of the operation candidate and an execution of the operation are automatically performed by using a prediction result of the operation to be performed next when the operation is performed. Therefore, the operation data includes time information about the operation interval. Specifically, in each operation, the time information after an operation before one operation is performed until the operation is performed is included in the operation data.

Figure 12:
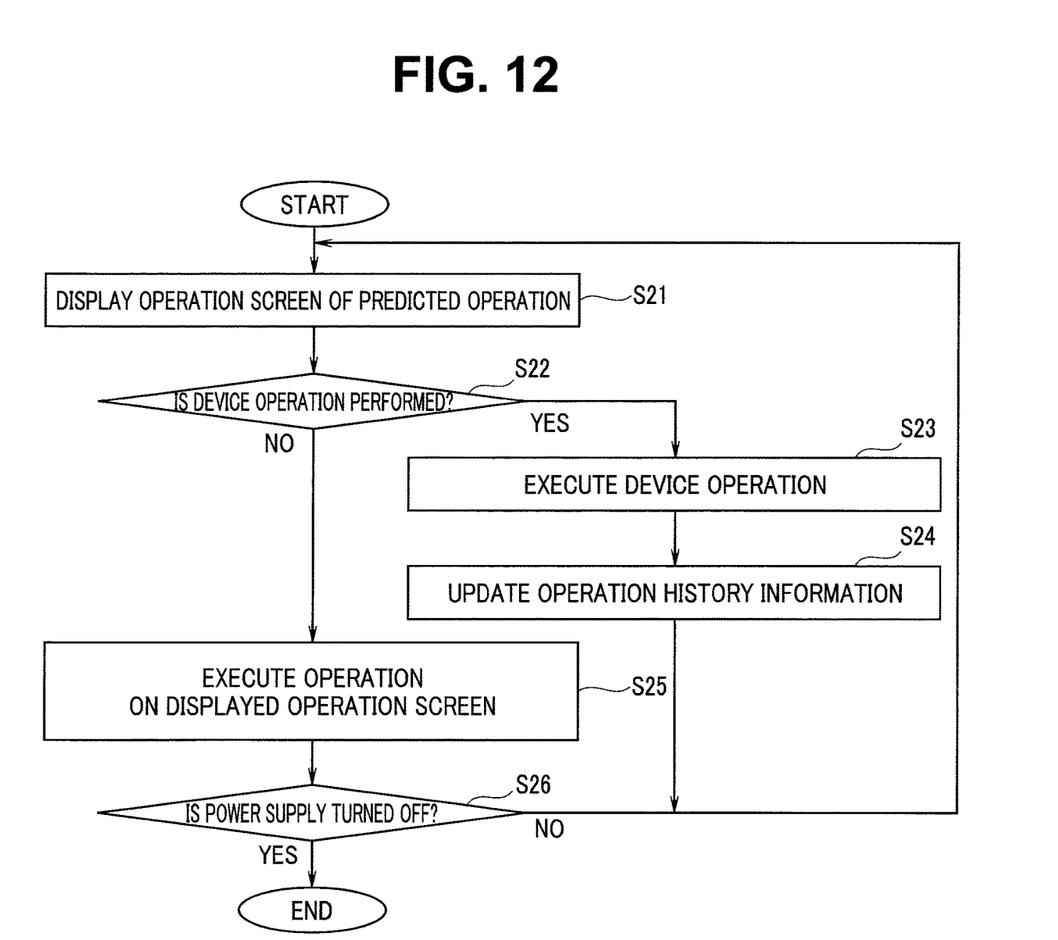
FIG. 12 is a flowchart showing an example of a flow of an automatic execution processing of an operation according to an exemplary embodiment.

FIG. 12 is a flowchart showing an example of a flow of an automatic execution processing of the operation according to the present embodiment. FIG. 12 is a flowchart in a case of using the operation history data.

After a user name and a procedure name are inputted to the operation panel apparatus 21, when a predetermined start switch is pushed, the process of FIG. 12 is started.

The operation history information table TBL or the neural network corresponding to the inputted user name and procedure name is selected.

When the start switch is pushed, a display of the operation screen of the operation predicted to be performed next is performed (S21). In the beginning, the operation screen of an operation to be performed first is displayed.

The control section 41 determines whether or not an operation is performed on the operation panel apparatus 21 within the set time, that is, determines whether or not the device operation is performed (S22). The set time is a time set for each operation screen. The set time is a time until the operation is performed on the operation screen after the operation screen is displayed. The time may be set for each operation screen by the user, the time may be set on the basis of time data until an operation is actually performed on the screen after the previous operation screen is displayed, or the time may be set, for example, by statistically calculating an average from the past operation data.

If the device operation is performed within the set time (S22: YES), the control section 41 executes the device operation (S23) and updates the operation history information (S24).

After the process of S24, the control section 41 uses the operation executed in the process of S23 as the operation performed currently and displays the operation screen of an operation predicted to be performed next (S21).

If the device operation is not performed within the set time (S22: NO), the control section 41 executes an operation on the operation screen to be displayed on the basis of the operation history data (S25). As a result, even if the device operation is not performed, the control section 41 executes the predicted operation in a suitable timing.

Accordingly, when an operation on the operation screen displayed on the display apparatus of the operation panel apparatus 21 is not performed until a predetermined timing, the process of S22 and S25 configures an operation execution section that executes the predicted operation.

Note that, after the process of S25, updating of the operation history information is not performed.

The control section 41 determines whether or not a power supply of the system controller 22 is turned off (S26), and if the power supply is turned off, the process ends. If the power supply is not turned off, the process returns to S21 and the process from S21 to S26 is repeated.

Accordingly, if the device operation is not performed (S22: NO), the control section 41 executes an operation to be performed next in the set timing (S25).

As described above, according to the present embodiment, the centralized control apparatus and the device operating method that are intended to be capable of smoothly performing various operations to be performed in a procedure can be provided.

The present invention is not limited to the above-described embodiments, and various changes and modifications can be made without departing from the scope of the present invention

What is claimed is:

1. A method comprising:
   predicting, when a first operation is performed on one device of a plurality of devices including a medical instrument, a second operation having a higher possibility to be performed after the first operation by using a neural network prepared based on past operation information performed on the plurality of devices; and
   displaying the predicted second operation on a display apparatus.

2. The method according to claim 1, further comprising:
   executing the second operation at a predetermined time after the predicted second operation on the operation screen is displayed on the display apparatus.

* * * * *